United States Patent [19]

Bundy

[11] 4,317,941
[45] * Mar. 2, 1982

[54] 2-DECARBOXY-2-HYDROXYMETHYL-TRANS-2,3-DIDEHYDRO-9-DEOXY-9-METHYLENE-PGF COMPOUNDS

[75] Inventor: Gordon L. Bundy, Portage, Mich.

[73] Assignee: The Upjohn Company, Kalamazoo, Mich.

[*] Notice: The portion of the term of this patent subsequent to Jul. 25, 1995, has been disclaimed.

[21] Appl. No.: 932,997

[22] Filed: Aug. 11, 1978

Related U.S. Application Data

[62] Division of Ser. No. 893,771, Apr. 5, 1978, Pat. No. 4,165,436.

[51] Int. Cl.³ ............... C07C 43/215; C07C 35/06
[52] U.S. Cl. ............... 568/646; 568/645; 568/644; 568/807; 568/838
[58] Field of Search ............... 568/807, 838, 644, 645, 568/646

[56] References Cited

U.S. PATENT DOCUMENTS 4,103,097  7/1978  Bundy ............... 568/807

OTHER PUBLICATIONS

Samuelsson et al., Advances in Prostaglandin and Thromboxane Research, vol. 1 (1976), pp. 483–493.

*Primary Examiner*—Bernard Helfin
*Attorney, Agent, or Firm*—Robert A. Armitage

[57] ABSTRACT

The present specification relates to novel 9-deoxy-9-methylene-trans-2,3-didehydro-PGF compounds with improved pharmacological properties. While these compounds are useful in inducing a wide variety of prostaglandin-like pharmacological effects, they are specifically useful as regulators of procreation and fertility.

22 Claims, No Drawings

2-DECARBOXY-2-HYDROXYMETHYL-TRANS-2,3-DIDEHYDRO-9-DEOXY-9-METHYLENE-PGF COMPOUNDS

The present application is a divisional application of Ser. No. 893,771, filed Apr. 5, 1978, now U.S. Pat. No. 4,165,436, issued Aug. 21, 1979.

The present invention relates to prostaglandin analogs, for which the essential material constituting disclosure therefor is incorporated by reference here from U.S. Pat. No. 4,165,436.

I claim:

1. A prostaglandin analog of the formula wherein $Y_1$ is trans-CH=CH-, -C≡C-, —$CH_2CH_2$—, or cis-CH=CH-;
wherein $M_1$ is or wherein $R_5$ is hydrogen or methyl;
wherein $L_1$ is or a mixture of and wherein $R_3$ and $R_4$ are hydrogen, methyl, or fluoro, being the same or different, with the proviso that one of $R_3$ and $R_4$ is fluoro only when the other is hydrogen or fluoro;
wherein g is 4, 5, or 6;
wherein $R_7$ is $$-(CH_2)_m-CH_3, \quad (1)$$

(2)

, or (3)

wherein h is zero, one, two, or three, wherein m is one to 5, inclusive, T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl, with the further proviso that $R_7$ is wherein T and s are as defined above, only when $R_3$ and $R_4$ are hydrogen or methyl, being the same or different.

2. A prostaglandin analog according to claim 1, wherein $R_7$ is 3. 2-Decarboxy-2-hydroxymethyl-trans-2,3-didehydro-9-deoxy-9-methylene-17-phenyl-18, 19,20-trinor-$PGF_1$, a prostaglandin analog according to claim 2.

4. A prostaglandin analog according to claim 1, wherein $R_7$ is 5. 2-Decarboxy-2-hydroxymethyl-trans-2,3-didehydro-9-deoxy-9-methylene-16-phenoxy-17,18,19,20-tetranor-$PGF_1$, a prostaglandin analog according to claim 4.

6. A prostaglandin analog according to claim 1, wherein $R_7$ is -$(CH_2)_m$-$CH_3$.

7. A prostaglandin analog according to claim 6, wherein m is 3.

8. A prostaglandin analog according to claim 7, wherein g is 4.

9. A prostaglandin analog according to claim 8, wherein $Y_1$ is -C≡C-.

10. 2-Decarboxy-2-hydroxymethyl-trans-2,3-didehydro-9-deoxy-9-methylene-13,14-didehydro-$PGF_1$, a prostaglandin analog according to claim 9.

11. A prostaglandin analog according to claim 8, wherein $Y_1$ is -$CH_2CH_2$-.

12. 2-Decarboxy-2-hydroxymethyl-trans-2,3-didehydro-9-deoxy-9-methylene-13,14-dihydro-$PGF_1$, a prostaglandin analog according to claim 11.

13. A prostaglandin analog according to claim 8, wherein $Y_1$ is trans-CH=CH-.

14. A prostaglandin analog according to claim 13, wherein at least one of $R_3$ and $R_4$ is fluoro.

15. 2-Decarboxy-2-hydroxymethyl-trans-2,3-didehydro-9-deoxy-9-methylene-16,16-difluoro-$PGF_1$, a prostaglandin analog according to claim 14.

16. A prostaglandin analog according to claim 13, wherein at least one of $R_3$ and $R_4$ is methyl.

17. 2-Decarboxy-2-hydroxymethyl-trans-2,3-didehydro-9-deoxy-9-methylene-16,16-dimethyl-$PGF_1$, a prostaglandin analog according to claim 16.

18. A prostaglandin analog according to claim 13, wherein $R_3$ and $R_4$ are both hydrogen.

19. A prostaglandin analog according to claim 18, wherein $R_5$ is methyl.

20. 2-Decarboxy-2-hydroxymethyl-trans-2,3-didehydro-9-deoxy-9-methylene-15-methyl-PGF$_1$, a prostaglandin analog according to claim 19.

21. A prostaglandin analog according to claim 20, wherein $R_5$ is hydrogen.

22. 2-Decarboxy-2-hydroxymethyl-trans-2,3-didehydro-9-deoxy-9-methylene-PGF$_1$, a prostaglandin analog according to claim 21.

* * * * *